United States Patent
Biggs et al.

(10) Patent No.: US 7,167,749 B2
(45) Date of Patent: Jan. 23, 2007

(54) ONE PIECE HEADER ASSEMBLY FOR AN IMPLANTABLE MEDICAL DEVICE

(75) Inventors: James C. Biggs, East Aurora, NY (US); David D. Warchocki, North Tonawanda, NY (US); David A. Faltisco, Blasdell, NY (US); George McNamara, North Tonawanda, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 505 days.

(21) Appl. No.: 10/701,849

(22) Filed: Nov. 5, 2003

(65) Prior Publication Data

US 2004/0093038 A1 May 13, 2004

Related U.S. Application Data

(60) Provisional application No. 60/423,787, filed on Nov. 5, 2002.

(51) Int. Cl.
*A61N 1/08* (2006.01)
(52) U.S. Cl. .......................................... 607/36; 607/37
(58) Field of Classification Search ................ 607/10, 607/36, 37, 27; 439/909
See application file for complete search history.

(56) References Cited

U.S. PATENT DOCUMENTS

| | | |
|---|---|---|
| 4,010,759 A | 3/1977 | Boer |
| 4,010,760 A | 3/1977 | Kraska et al. |
| 4,041,956 A | 8/1977 | Purdy et al. |
| 4,057,068 A | 11/1977 | Comben |
| 4,182,345 A | 1/1980 | Grose |
| 4,254,775 A | 3/1981 | Langer |
| 4,262,673 A | 4/1981 | Kinney et al. |
| 4,471,783 A | 9/1984 | Buffet |
| 4,764,132 A | 8/1988 | Stutz, Jr. |
| 5,070,605 A | 12/1991 | Daglow et al. |
| 5,076,270 A | 12/1991 | Stutz, Jr. |
| 5,086,773 A | 2/1992 | Ware |
| 5,103,818 A | 4/1992 | Maston et al. |
| 5,282,841 A | 2/1994 | Szyszkowski |
| 5,336,246 A | 8/1994 | Dantanarayana |
| 5,549,653 A | 8/1996 | Stotts et al. |
| 5,643,328 A | 7/1997 | Cooke et al. |
| 5,662,692 A * | 9/1997 | Paspa et al. .................. 607/37 |
| 5,741,313 A | 4/1998 | Davis et al. |
| 5,755,743 A | 5/1998 | Volz et al. |
| 5,871,514 A | 2/1999 | Wiklund et al. |
| 5,980,973 A | 11/1999 | Onyekaba et al. |

(Continued)

FOREIGN PATENT DOCUMENTS

EP    0 006 281    1/1980

*Primary Examiner*—Robert E. Pezzuto
*Assistant Examiner*—Tammie K. Heller
(74) *Attorney, Agent, or Firm*—Michael F. Scalise

(57) ABSTRACT

A header assembly mounted to a medical device for connecting to at least one conductor lead terminating at a target organ or portion of the body intending to be assisted is described. The header assembly comprises a body of polymeric material supporting at least one unitary conductor wire. The conductor wire connects between a feedthrough wire exiting the medical device and a terminal block into which the conductor lead plugs. Various structures are described for connecting the conductor wire to the feedthrough wire.

23 Claims, 9 Drawing Sheets

U.S. PATENT DOCUMENTS 6,026,325 A 2/2000 Weinberg et al.
6,052,623 A 4/2000 Fenner et al.

6,817,905 B2 * 11/2004 Zart et al. .................. 439/736

* cited by examiner

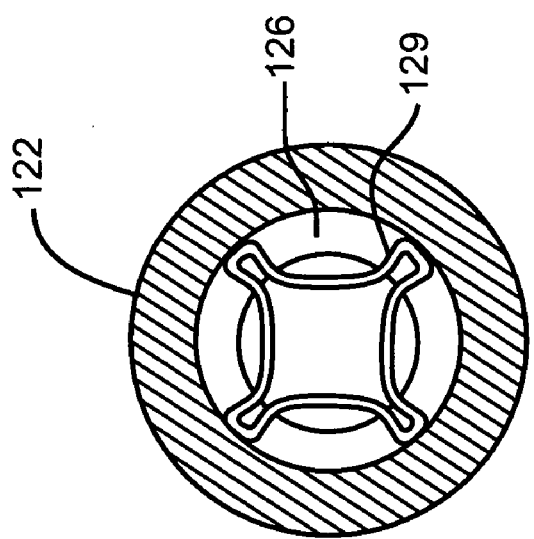
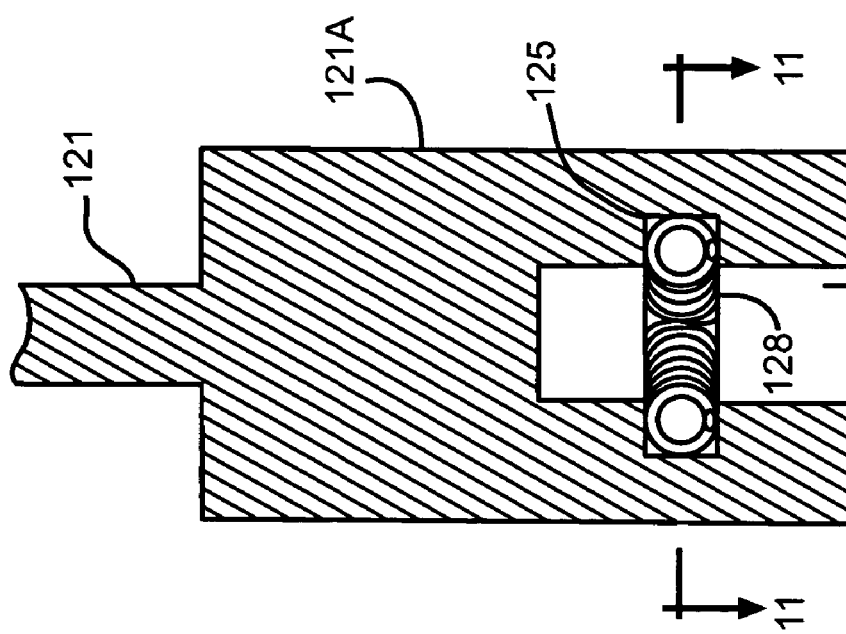

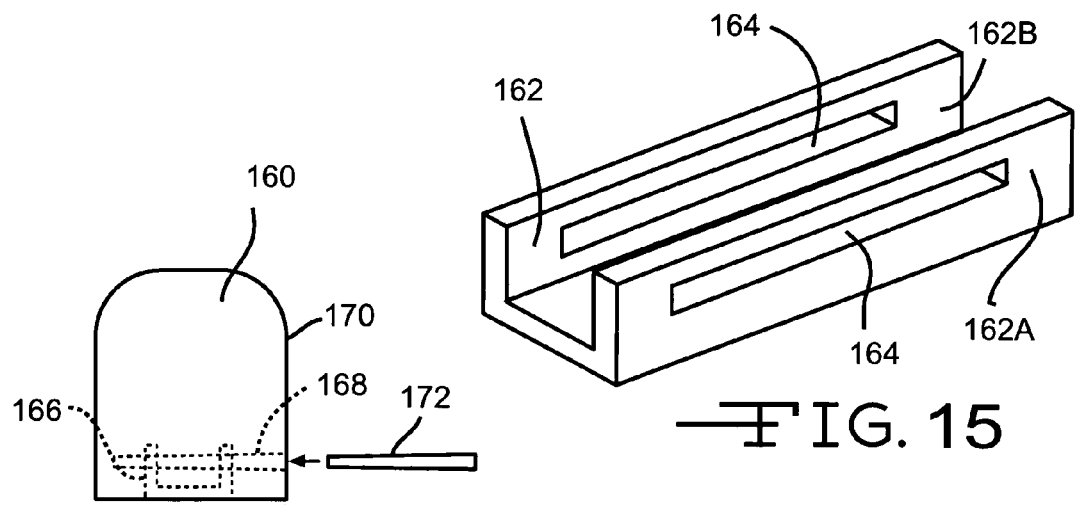
FIG. 15
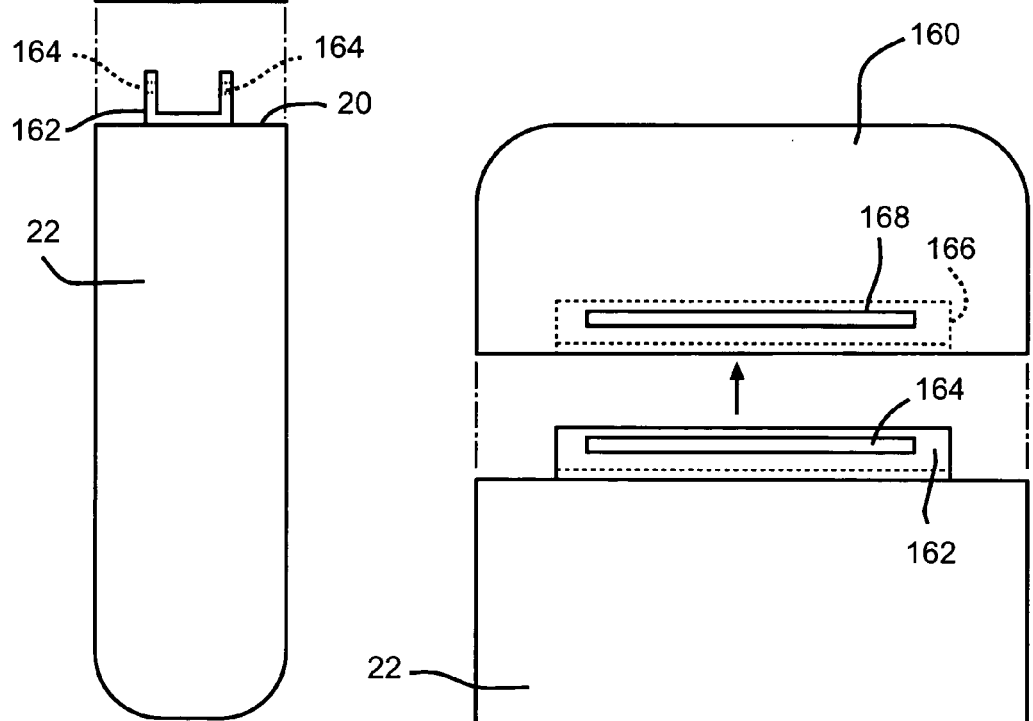
FIG. 16
FIG. 17

ONE PIECE HEADER ASSEMBLY FOR AN IMPLANTABLE MEDICAL DEVICE

CROSS REFERENCE TO RELATED APPLICATIONS

This application claims priority based on provisional applications Ser. No. 60/423,787, filed Nov. 5, 2002.

BACKGROUND OF THE INVENTION

1. Field of the Invention

The invention relates to a one-piece header assembly for connecting an implantable medical device to a body organ assisted by the medical device. The header assembly includes terminal blocks electrically connected to the distal end of intermediate conductor wires supported in the header. The proximal end of the intermediate conductor wires comprise a quick connect structure for connecting to feedthrough wires or pins exiting the medical device. Electrical leads are plugged into the terminal blocks to establish continuity from the medical device to a tip of the electrical leads inserted into a body tissue.

2. Prior Art

Implantable medical devices have feedthrough conductors in the form of pins or wires connected to the internal components of the medical device. The feedthrough wires extend through a wall of the medical device housing and are electrically insulated therefrom by a ceramic-to-metal seal or a glass-to-metal seal. Electrical continuity to a conductor lead attached to the body being assisted is established by connecting intermediate conductor wires supported by a polymeric header mounted on the medical device to the feedthrough wires and terminal blocks in the molded header. The terminal blocks then provide for plugging the conductor lead into the molded polymeric header. Examples of this type of header assembly are shown in U.S. Pat. No. 4,254,775 to Langer, U.S. Pat. No. 4,262,673 to Kinney et al., U.S. Pat. No. 4,764,132 to Stutz, Jr., U.S. Pat. No. 5,282,841 to Szyszkowski and U.S. Pat. No. 5,336,246 to Dantanarayana. However, what is needed is a quick and reliable connection between the feedthrough wires from the medical device and the intermediate conductor wires supported by the molded header. The present invention connection structures are improvements over those shown by the prior art patents.

SUMMARY OF THE INVENTION

The present invention is, therefore, directed to a header assembly for a medical device. The header assembly provides electrical connection between feedthrough wires extending from inside the medical device to a conductor lead connected to the body organ or tissue being assisted. Several different embodiments of header assemblies are described comprising structures for securing the feedthrough wires from the medical device to conductor wires in the molded header. The conductor wires are, in turn, connected to terminal blocks into which the lead wires from the body tissue are plugged into.

These features of the present invention will be apparent upon consideration of the following detailed description thereof presented in connection with the following drawings.

BRIEF DESCRIPTION OF THE DRAWINGS

FIG. 10A illustrates an alternate embodiment of a conductor wire 121 having a unitary proximal end 121A supporting a coil spring 128 in an inner annular groove 125 thereof.

FIG. 11A illustrates an alternate embodiment of an leaf spring 129 supported in an inner annular groove 126 provided at the proximal end of a conductor wire.

FIG. 15 is a perspective view of another embodiment of a bracket 162 for securing a polymeric header 160 to the medical device 122.

FIGS. 16 and 17 are side and front elevational views, respectively, showing the header 160 being secured to the medical device 22.

DETAILED DESCRIPTION OF THE PREFERRED EMBODIMENTS

Figure 1:
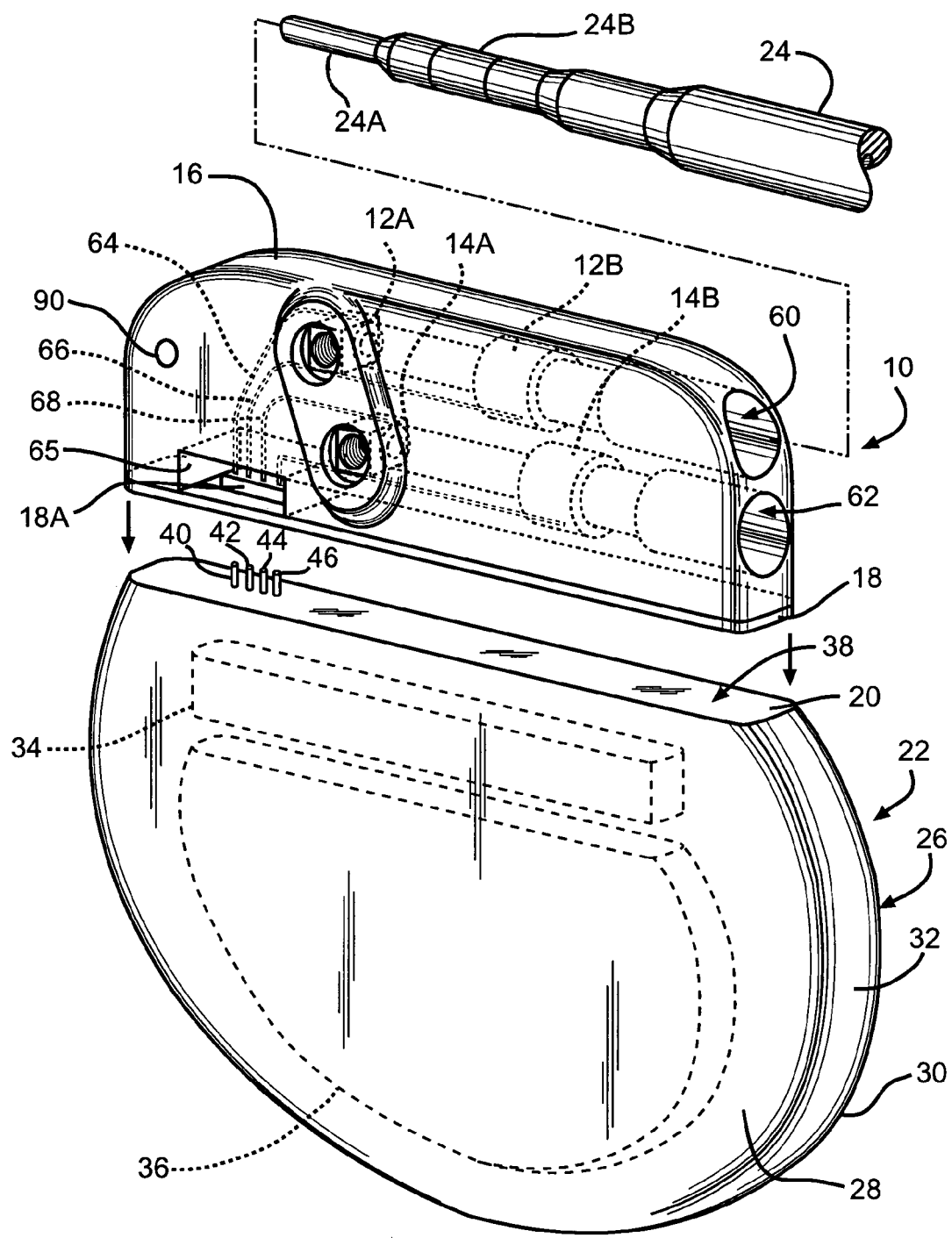
FIG. 1 is an exploded view of a header assembly 10 mounted on an implantable medical device 18 according to the present invention.
Figure 2:
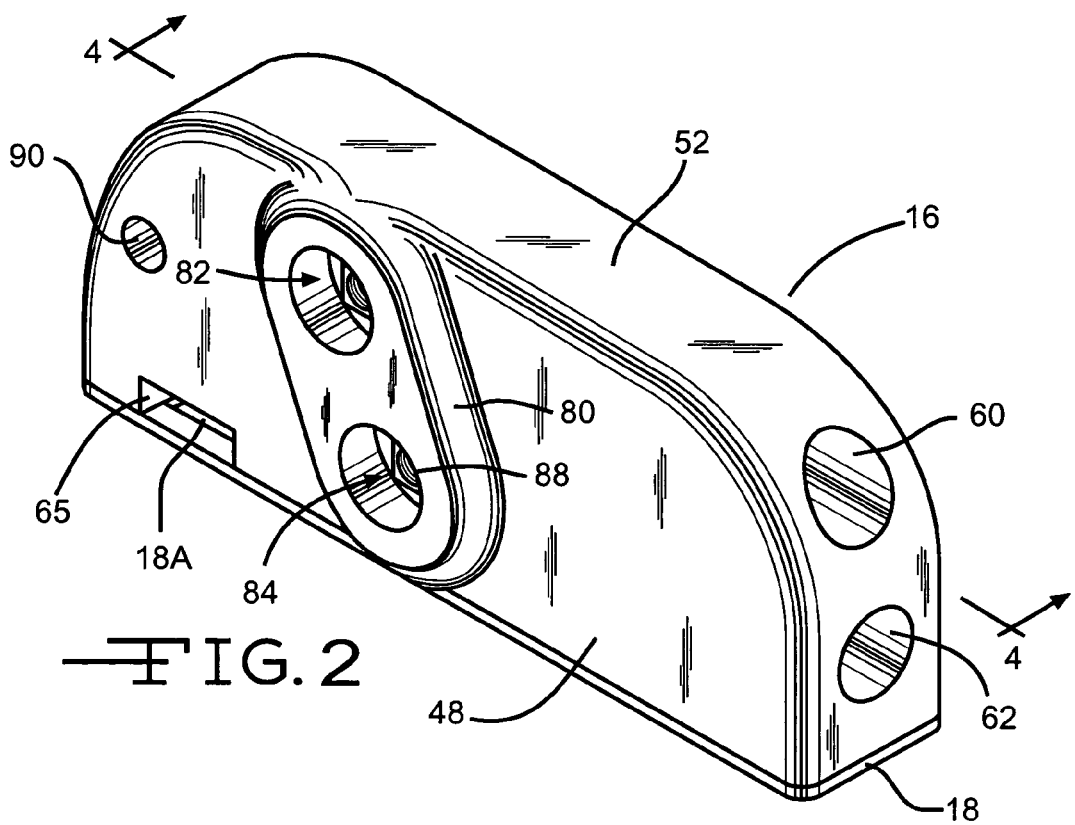
FIG. 2 is a perspective view of the header assembly 10 shown in FIG. 1.

Referring now to the drawings, FIGS. 1 to 6 illustrate a header assembly 10 according to the present invention comprising two pairs of terminal blocks 12A, 12B and 14A, 14B partially surrounded by a header 16 comprising a body of molded polymeric material mounted on a support plate 18. The support plate 18, in turn, is mounted on the header portion 20 of an implantable medical device 22. The terminal block pairs 12A, 12B and 14A, 14B each provide for connecting the lead 24 for a co-axial conductor wire from the medical device to a body tissue. The implantable medical device 22 is exemplary of any one of a number of known assist devices such as cardiac defibrillators, cardiac pacemakers, drug pumps, neurostimulators, hearing assist devices, and the like.

The implantable medical device 22 comprises a housing 26 of a conductive material, such as of titanium or stainless steel. Preferably, the medical device housing 26 is comprised of mating clam shells in an overlapping or butt welded construction, as shown in U.S. Pat. No. 6,613,474 to Frustaci et al., which is assigned to the assignee of the present invention and incorporated herein by reference. The housing 26 can also be of a deep drawn, prismatic and cylindrical design, as is well known to those skilled in the art.

The housing 26 is shown in an exemplary form comprising first and second planar major face walls 28 and 30 joined together by a sidewall 32 and the header 20. The sidewall 32 curves from one end of the header 20 to the other end and is generally arcuate from face wall 28 to face wall 30. The preferred mating clam shells of housing 26 are hermetically sealed together, such as by laser or resistance welding, to provide an enclosure for the medical device including its control circuitry 34 and a power supply 36, such as a battery (the control circuitry and power supply are shown in dashed lines in FIG. 1). The power supply 36 is connected to the control circuitry 34 by electrical leads (not shown). There may also be a capacitor for a medical device such as a defibrillator.

The header 20 of housing 26 has a planar upper surface 38 providing at least four openings through which respective feedthrough wires 40, 42, 44, and 46 pass. The feedthrough wires extend from a distal end positioned inside the housing 26 connected to the control circuitry 34 to respective proximal ends spaced above the header upper surface 38. The feedthrough wires 40, 42, 44, and 46 are electrically insulated from the housing 26 by respective ceramic-to-metal seals or glass-to-metal seals (not shown), as are well known by those skilled in the art.

Figure 3:
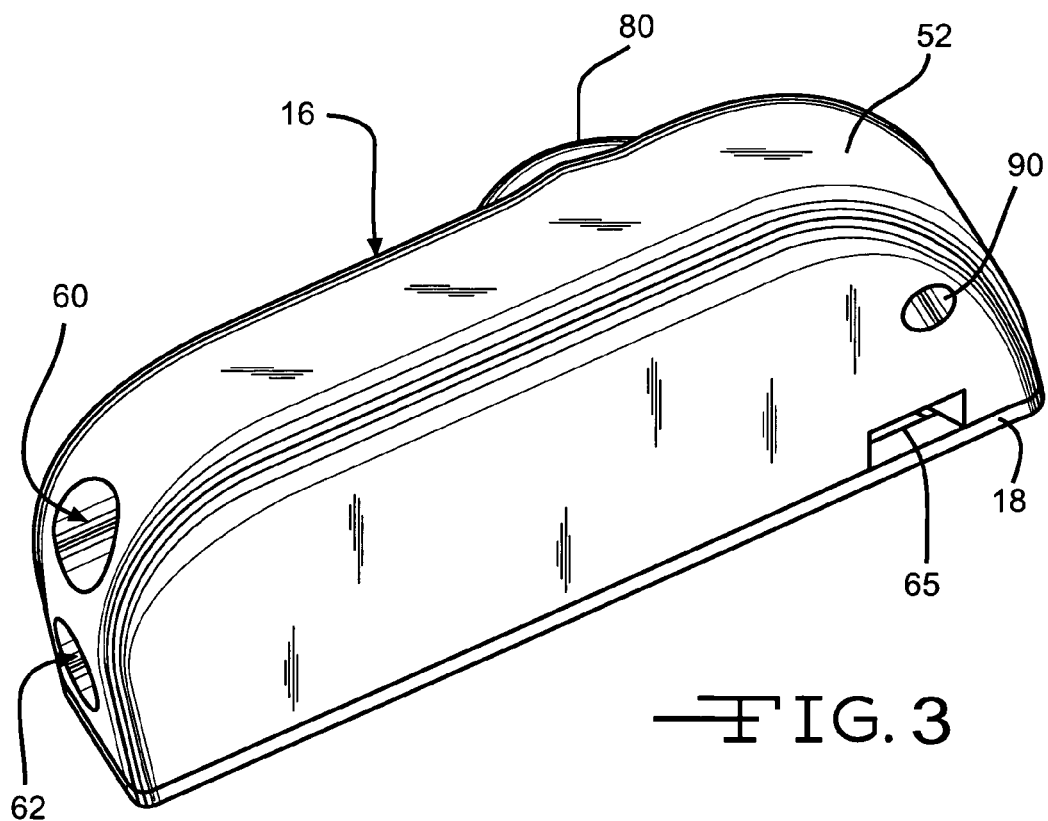
FIG. 3 is another perspective view of the header assembly shown in FIG. 1.

As shown in FIG. 3, the terminal block pairs 12A, 12B and 14A, 14B are aligned in a co-axial relationship and encased in the polymeric material of the molded header 16. The molded header 16 comprises spaced apart front and back walls 48 and 50 extending to a curved upper wall 52 and a generally planar bottom wall 54. The bottom wall 54 is supported on the upper surface 56 of support plate 18 and retained in place by encasing a peripheral undercut 58 of the support plate. In an alternate embodiment, the support plate 18 is replaced by a ring (not shown) having either an outer peripheral undercut or an inner peripheral undercut, or both.

Those skilled in the art will readily understand that the exact shape of the molded header is exemplary. In fact, the molded header can have a myriad of different shapes only limited by the design specifications of the associated medical device and its intended use.

Each terminal block 12A, 12B, 14A, 14B has an internal cylindrically shaped bore. The terminal block pairs 12A, 12B and 14A, 14B have their internal bores aligned along the longitudinal axis of a respective bore 60, 62 leading into the polymeric header 16 from the curved upper wall 52. The structure of the bores 60, 62 will be described in detail with respect to the former bore. However, it is understood that a similar structure exists for bore 62.

In that respect, the header assembly bore 60 has a first portion 60A of a first diameter sized to receive a distal portion 24A of the conductor lead 24, a second, intermediate portion 60B of a second, greater diameter sized to receive a proximal portion 24B of the lead and a third portion 60C of a still greater diameter than the intermediate portion. Frustoconically shaped portions lead from one bore portion to the next larger bore portion. The terminal blocks 12A, 12B have lead openings of diameters somewhat larger than the first and second bore portions 60A, 60B so that the conductor lead 24 is received therein in a tight fitting, electrically stable connection.

Figure 4:
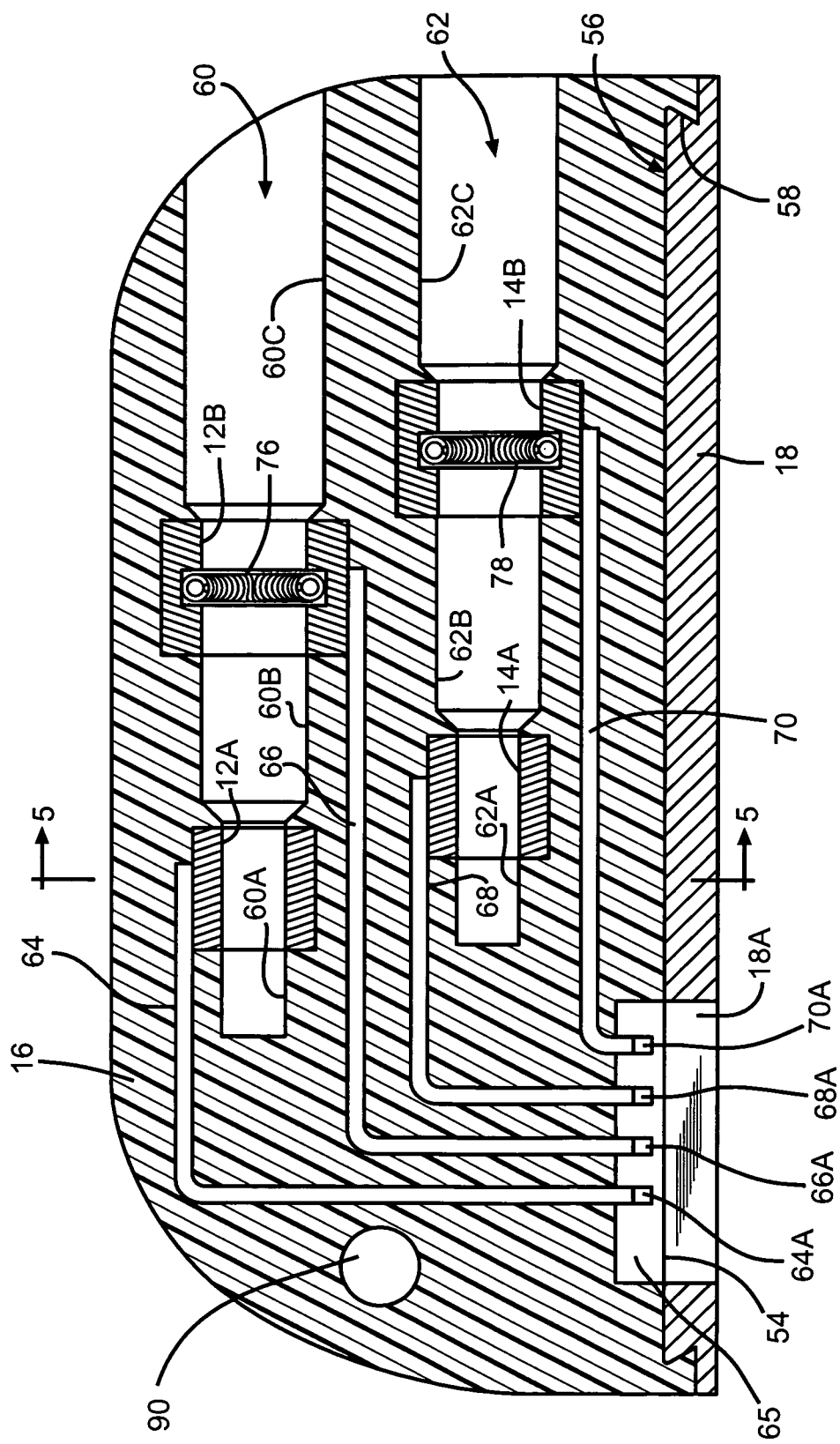
FIG. 4 is a cross-sectional view taken along line 4—4 of FIG. 2.
Figure 5:
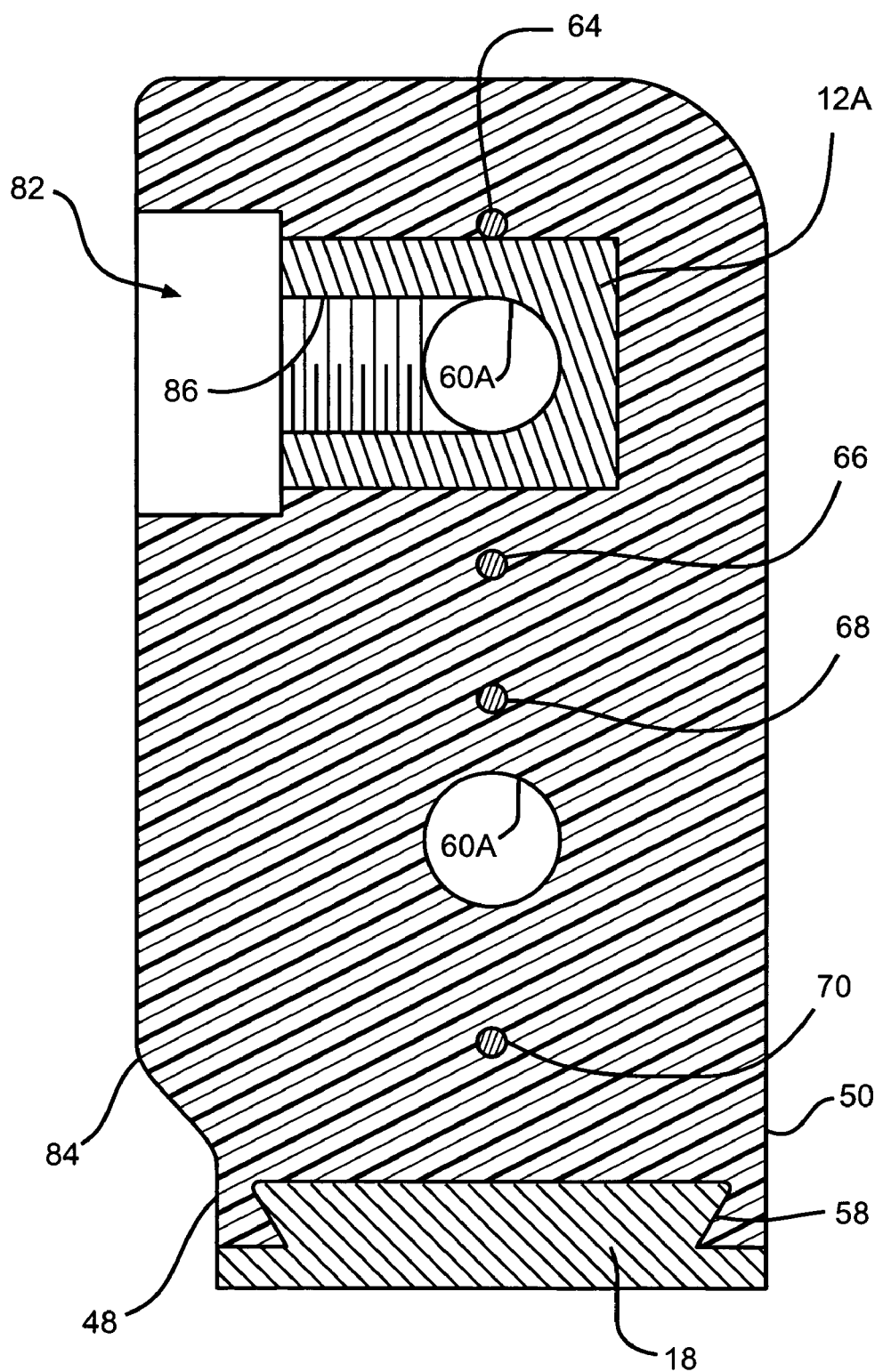
FIG. 5 is a cross-sectional view taken along line 5—5 of FIG. 4.

As shown in FIG. 4, each terminal block 12A, 12B, 14A and 14B is connected to an intermediate conductor wire that provides electrical conductivity between the block and its associated feedthrough wires from the medical device. More specifically, intermediate conductor wire 64 is a unitary member having a distal end electrically secured, such as by welding, to the outer wall of terminal block 12A. This wire 64 has a bend along its length and leads to a proximal end 64A residing in an inlet 65 in the bottom wall 54 of the header 16. The intermediate conductor wire 64 has a generally circular cross-section perpendicular to its longitudinal axis except at its proximal end. There, the wire has a step 64A about halfway through its diameter. The step 64A provides a lap joint structure for securing the intermediate conductor wire 64 to feedthrough wire 40, as will be described in detail presently.

In a similar manner, terminal block 12B is electrically connected to the distal end of intermediate conductor wire 66. The proximal end of wire 66 residing in the inlet 65 has a step 66A. The step 66A provides a lap joint for securing the intermediate conductor wire 66 to feedthrough wire 42.

Terminal block 14A is electrically connected to the distal end of intermediate conductor wire 68. The proximal end of wire 68 has a step 68A residing in inlet 65 for securing the intermediate conductor wire to feedthrough wire 44.

Terminal block 14B is electrically connected to the distal end of intermediate conductor wire 70. The proximal end of wire 70 has a step 70A residing in inlet 65 for securing the intermediate conductor wire to feedthrough wire 46.

While header 16 is illustrated having two pairs of terminal blocks, this is for illustrative purposes only. Those skilled in the art will realize that the header can have one pair of terminal blocks, or more than two pairs. Also, the terminal blocks need not be provided in pairs. Instead, a header bore can be in communication with only one terminal block, or with more than two aligned blocks.

Terminal blocks 12B and 14B are each provided with respective inner annular grooves 72 and 74. Respective collapsible coil springs 76, 78 are nested in the grooves 72, 74 to help ensure that the terminal blocks 12B, 14B are electrically connected to the conductor leads 24 received in the bores 60, 62.

The front wall 48 of the molded header 16 is provided with an oval shaped raised land 80. A pair of passageways 82 and 84 enter the raised land 80 to communicate with the respective terminal blocks 12A, 14A. The passageways 82, 84 are aligned perpendicularly with the longitudinal axes of the bores 60, 62. Passageway 82 leads to a threaded aperture 86 (FIGS. 1, 2 and 5) in terminal block 12A that receives a setscrew (not shown). The setscrew contacts the distal portion 24A of the conductor lead 24 to prevent loss of electrical contact between the lead and the terminal blocks 12A, 12B. Similarly, passageway 84 extends to a threaded aperture 88 in the sidewall of terminal block 14A that receives a setscrew (not shown) to maintain electrical continuity between the lead and the terminal blocks 14A, 14B.

The thusly described molded header 16 is mounted on the medical device 22 with the support plate 18 contacting the upper surface 38 of the header 20. The support plate 18 has an opening 18A (FIGS. 1, 2 and 4) through which the feedthrough wires 40, 42, 44 and 46 extend. The support plate 18 and header 20 are both of a conductive metal and welding is typically used to join them together. With the molded header 16 secured to the medical device 22, the feedthrough wire 40 is of a length to overlap the step 64A at the proximal end of intermediate conductor wire 64 residing in inlet 65. Welding the feedthrough wire 40 to the step 64A of conductor wire 64 then makes electrical connection. In this manner, there are only two connections between the medical device and the terminal block. One is where the feedthrough wire 40 connects to the step 64A and the other is where the distal end of the intermediate conductor wire 64 connects to the terminal block 12A.

A similar electrical connection is made by welding feedthrough wire 42 to step 66A of conductor wire 66, feedthrough wire 44 to step 68A of conductor wire 68 and feedthrough wire 46 to step 70A of conductor wire 70. In this manner, electrical continuity is established between the control circuitry 34 of the medical device 22 and the terminal blocks 12A, 12B, 14A and 14B through respective intermediate conductor wires 64, 66, 68 and 70.

Inlet 65 in the molded header 16 (FIGS. 1 to 4) where the feedthrough wires 40, 42, 44 and 46 and the proximal ends 64A, 66A, 68A and 70A of the intermediate conductor wires are connected together is then back filled with a polymeric material. A suitable one is a silicon-based material. This prevents body fluids from coming into contact with these electrical connections.

In use, the medical device is positioned in a body, such as a human or animal, to assist a body function. A suture opening 90 is provided in the molded header 16 to aid in securing the medical device 22 inside the body. The physician then plugs a conductor lead 24 into each bore 60, 62 in molded header 16. The distal end (not shown) of the co-axial conductor opposite that of the lead 24 has already been positioned in a body tissue, such as a heart muscle, for transmitting physiological information to the medical device and for administering a medical theory as needed.

An example of this is in a cardiac defibrillator where the medical device may monitor the heart rate for extended periods of time. When a potentially fatal irregular, rapid heartbeat known as tachyarrhythmia is detected, the defibrillator delivers an electrical shock to the heart. The electrical shock is transmitted from the control circuitry 34 through the feedthrough wires 40, 42, 44 and 46 and intermediate conductor wires 64, 66, 68 and 70. These conductors are electrically connected to the terminal blocks 12A, 12B, 14A and 14B into which the conductor leads 24 are plugged.

Figure 6:
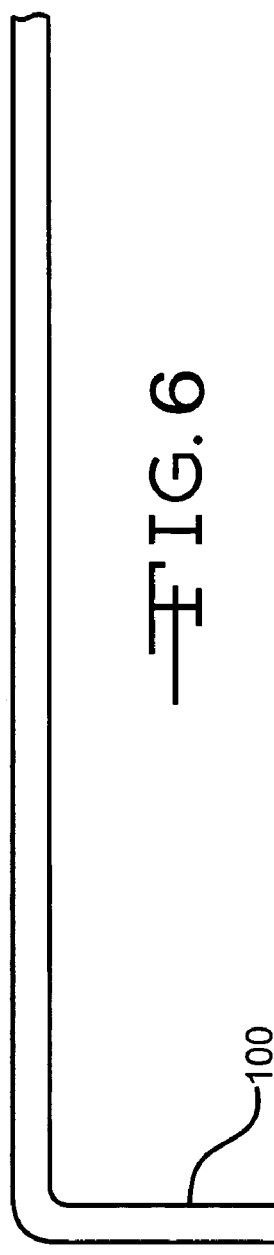
FIG. 6 is a perspective view of an alternate embodiment of an intermediate conductor lead 100.
Figure 7:
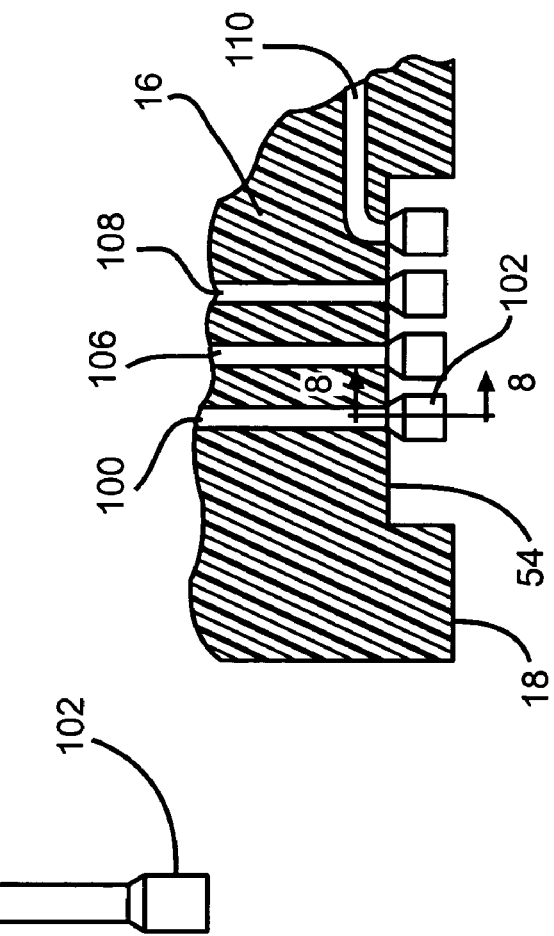
FIG. 7 is a partial cross-sectional view of the header 16 supporting a plurality of conductor leads 100, 106, 108 and 110.
Figure 8:
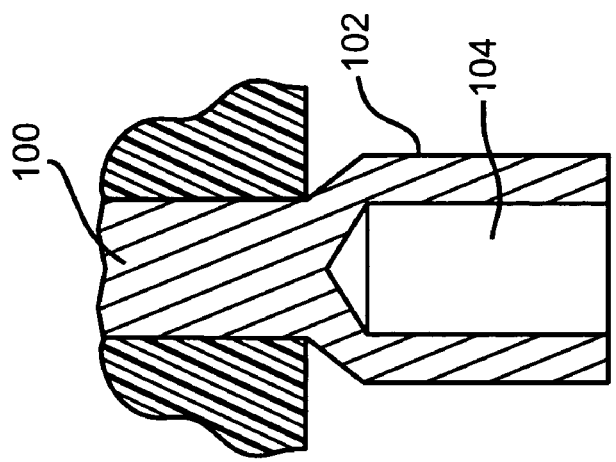
FIG. 8 is a cross-sectional view taken along line 8—8 of FIG. 7.

FIGS. 6 to 8 show an alternate embodiment of an intermediate conductor wire 100 according to the present invention. Conductor wire 100 is useful in lieu of, or in combination with, the previously described conductor wires 64, 66, 68 and 70. For example, terminal blocks 12A and 12B could be connected to an intermediate terminal wire of the structure 64 and 66 while terminal blocks 14A and 14B could be connected to intermediate conductor wire 100.

In any event, conductor wire 100 is preferably a unitary member having a circular cross-section perpendicular to its length extending from a distal end (not shown) electrically secured to a terminal block, for example block 12A, to an opposite proximal end 10A. The proximal end 100A of the conductor wire 100 resides in the inlet 65 of the molded header 16. The proximal end 100A comprises a head 102 of a larger diameter than the remaining length of the wire 100. The head 102 is a cylindrically shaped portion of a length somewhat less than the depth of inlet 65. A bore 104 is provided in head 102 aligned along the longitudinal axis thereof.

FIG. 7 shows the molded polymeric header 16 supporting four conductor wires 100, 106, 108 and 110 corresponding to the feedthrough wires 40, 42, 44 and 46. The feedthrough wires are received inside the bore 104 of head 102 of the conductor wires with the header 16 mounted on the medical device 22. The conductor wires and feedthrough wires are then joined together such as by welding. A silicon-based material (not shown) is used to backfill inlet 65 in molded header 16.

Figure 10:
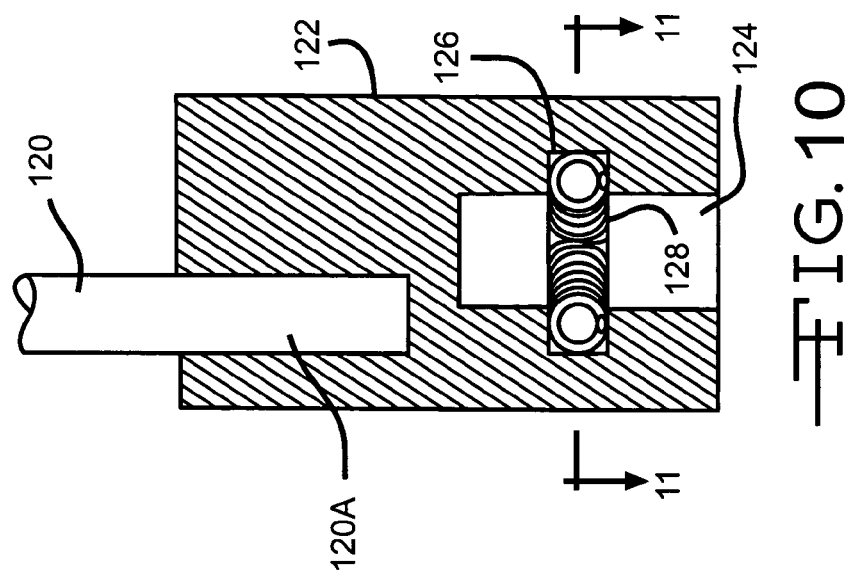
FIG. 10 is a cross-sectional view of conductor wire 120 and its associated conductor block 122.
Figure 11:
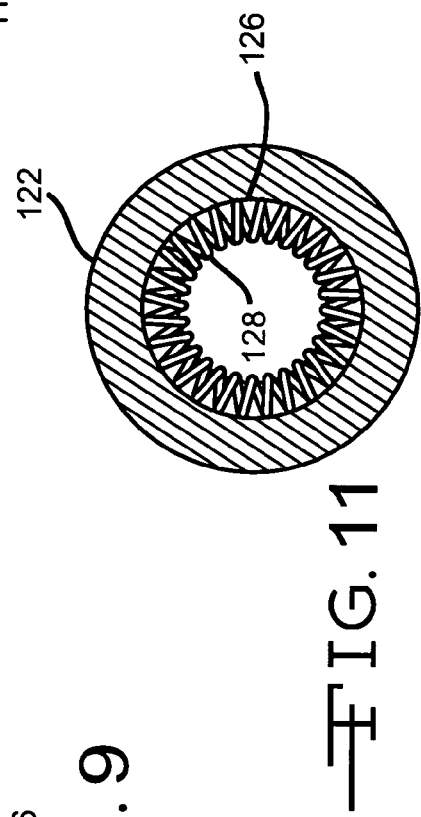
FIG. 11 is a cross-sectional view taken along line 11—11 of FIG. 10.
Figure 9:
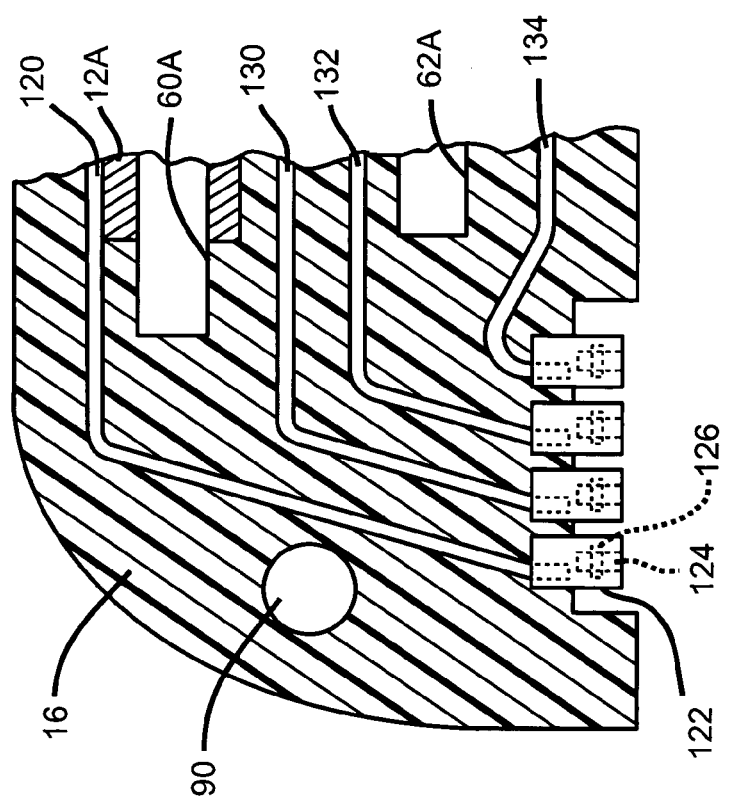
FIG. 9 is a partial cross-sectional view of header 16 supporting a plurality of intermediate conductor wires 120, 132, 134 and 136 accordingly to another embodiment of the invention.

FIGS. 9 to 11 show another embodiment of an intermediate conductor wire 120 according to the present invention. As with conductor wire 100, conductor wire 120 is useful in lieu of, or along with, the previously described conductor wires. Conductor wire 120 has a circular cross-section perpendicular to its length extending from a distal end (not shown) electrically secured to a terminal block, for example block 12A, to an opposite proximal end 120A. The end 120A resides in the inlet 65 of the molded polymeric header 16 and is received in a bore in a connector block 122. The conductor wire 120 and connector block 122 are preferably welded together. A coaxial bore 124 extends part way into the length of conductor block 122. An annular groove 126 provided in the sidewall of bore 124 has an annular coil spring 128 nested therein.

FIG. 9 shows the molded header 16 supporting four conductor wires 122, 130, 132, and 134 corresponding to the feedthrough wires 40, 42, 44 and 46. The feedthrough wires are received inside the bore 124 of the conductor block 122 of each of the conductor wires with the header 16 mounted on the medical device 22. There is no need to join the conductor wires and feedthrough wires by welding. Instead, the coil spring 128 provided sufficient conductivity between the feedthrough wires and the connector block 122 welded to the end 120A of the intermediate connector wire 120. A silicon-based material (not shown) is used to backfill the inlet 65 in the molded header 16.

As shown in FIG. 10A, it is further within the scope of the present invention that the conductor wire 120 and connector block 122 are unitary. Conductor wire 121 has a circular cross-section perpendicular to its length extending from a distal end (not shown) electrically secured to a terminal block, for example block 12A, to an opposite proximal head 121A. The proximal head 121A of conductor wire 121 resides in the inlet 65 of the molded polymeric header 16 and includes a coaxial bore 123 extending part ways into its length. An annular groove 125 provided in the sidewall of bore 123 has a coil spring 128 nested therein. In all other respects, conductor wire 121 functions in a similar manner as the previously described wire 120 and connector block 122.

It is also within the scope of the present invention that the spring need not be of a coil structure. As shown in FIG. 11A, the annular groove 126 provided in the sidewall of bore 124 supports an annular leaf spring 129 nested therein.

Figure 12:
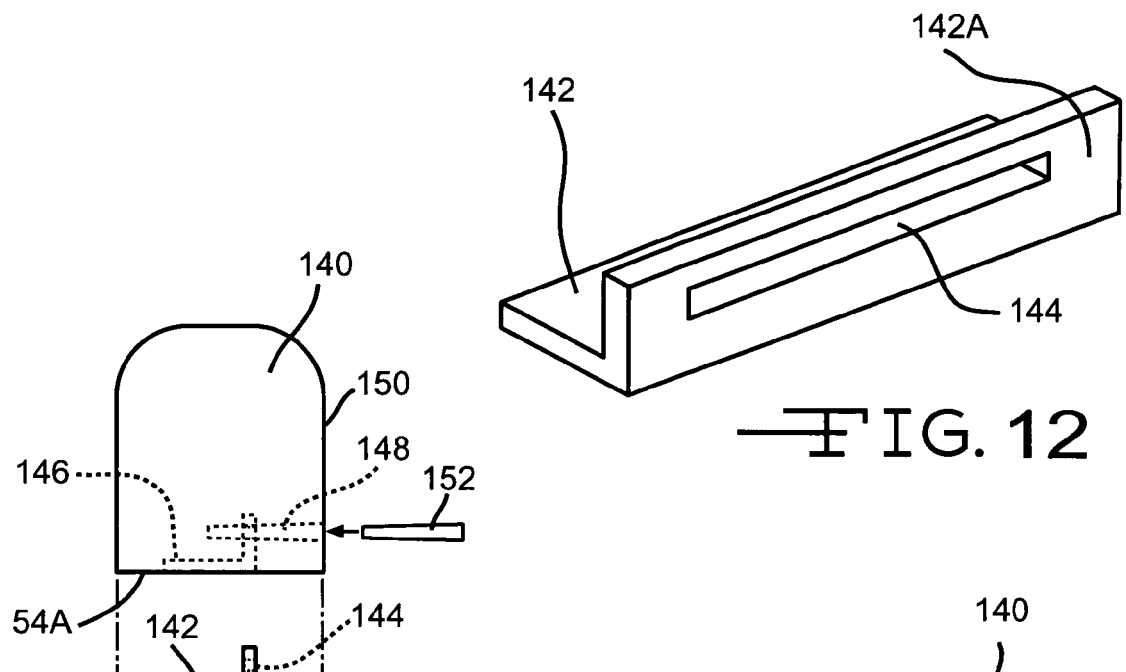
FIG. 12 is a perspective view of one embodiment of a bracket 142 for securing a polymeric header 140 to the medical device 22.
Figure 13:
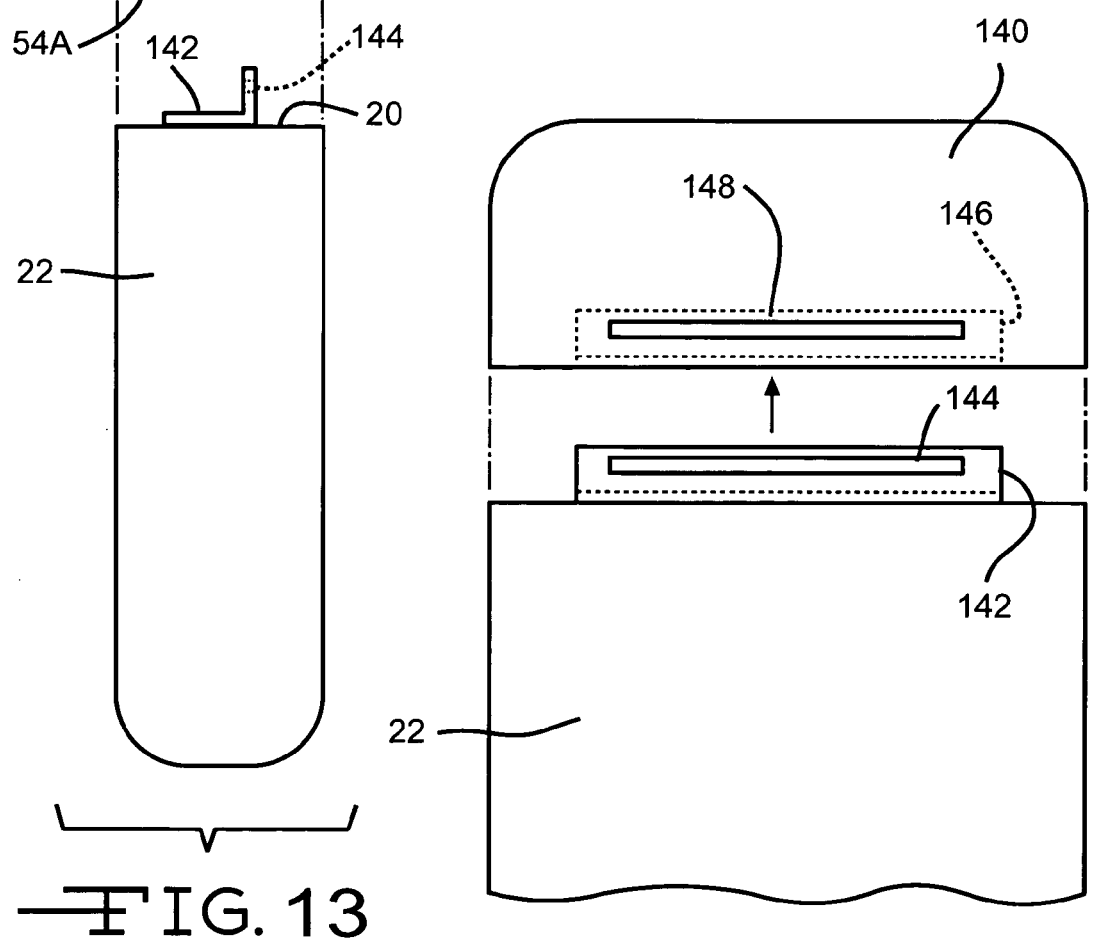
FIGS. 13 and 14 are side and front elevational views, respectively, showing the header 140 being secured to the medical device 22.
Figure 14:
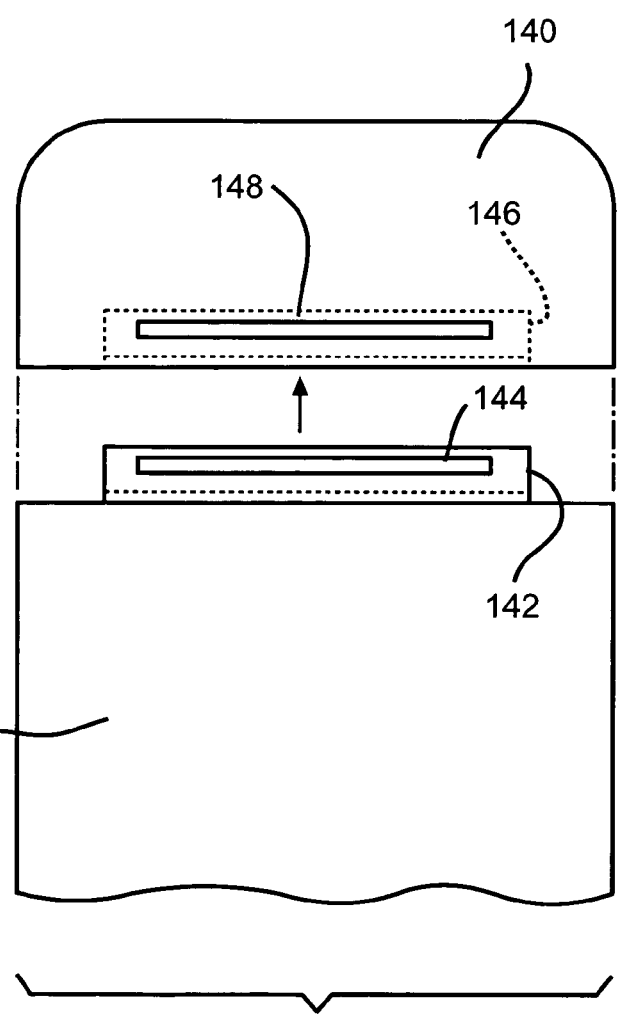

FIGS. 12 to 14 illustrate an alternate embodiment of a structure for securing a polymeric header 140 to the medical device 22. Polymeric header 140 is similar to the previously described header 16 except it is not molded to an undercut of a support plate. Instead, the header 20 of the medical device supports an L-shaped bracket 142, preferably of a metal such as titanium or stainless steel, having an upstanding wall 142A provided with an elongated slot 144. The longitudinal axis of slot 144 is parallel to the planar upper surface 56 of the medical device header 20. The bottom wall 54A of header 140 is provided with an inlet 146 that matches the shape of bracket 142. A lateral inlet 148 is provided in the sidewall 150 of header 140 and intersects with inlet 146. When the molded header 140 is mounted on the medical device 22, the bracket 142 is received in the inlet 146. In this position, the lateral inlet 148 is aligned with slot 144. As shown in FIG. 13, a wedge 152, preferably of a metal such as that of the bracket 142, is moved into the lateral inlet 148 and bracket slot 144 to pin or secure the header and medical device together. The wedge can also be of a polymeric material.

FIGS. 15 to 17 illustrate an alternate embodiment of a structure for securing a polymeric header 160, similar to the previously described header 140, to the medical device 22. The medical device header 20 supports a U-shaped bracket 162, preferably of a metal such as titanium or stainless steel, having a pair of upstanding sidewalls 162A and 162B, each provided with an elongated slot 164. The longitudinal axes of the slots 164 are parallel to the planar upper surface 56 of the medical device header 20. The bottom wall 54B of the molded header 160 is provided with an inlet 166 that matches the shape of bracket 162. A lateral inlet 168 is provided in the sidewall 170 of header 160 and intersects with inlet 164. When the header 160 is mounted on the medical device 22, the bracket 162 is received in the inlet 166. In this position, the lateral inlet 168 is aligned with slots 164. As shown in FIG. 16, a metal or polymeric wedge 172 is moved into the lateral inlet 168 and bracket slots 164 to secure the header 160 and medical device 22 together.

Now, it is therefore apparent that the present invention accomplishes its intended objects. While embodiments of the present invention have been described in detail, that is for the purpose of illustration, not limitation.

What is claimed is:

1. A header assembly for connecting an implantable medical device to a conductor lead terminating at a body organ intended to be assisted by the medical device comprising a housing containing control circuitry, at least one electrical energy storage device, and at least one feedthrough wire extending from the control circuitry and through a wall of the housing, the header assembly comprising:
    a) a body mountable on the housing for the medical device, wherein the body has a sidewall extending to a bottom wall disposable immediately adjacent to the medical device housing and wherein a connection inlet is provided in the body sidewall extending to the bottom wall at the sidewall;
    b) at least one terminal supported by the body, wherein the terminal is directly connectable to the conductor lead; and
    c) an intermediate conductor supported by the body, the intermediate conductor having a distal end connected to the terminal and a proximal end comprising a step residing in the connection inlet in the body and there being securable to the feedthrough wire in a lap joint construction.

2. The header assembly of claim 1 wherein the body is of a polymeric material.

3. The header assembly of claim 1 wherein the body includes a first inlet that receives a bracket secured to the housing and a second inlet and wherein with the bracket received in the first inlet, a wedge is receivable in the second inlet and a bracket inlet to secure the header assembly to the medical device.

4. The header assembly of claim 1 wherein the housing for the medical device comprises mating first and second clam shells.

5. The header assembly of claim 1 wherein the medical device is selected from the group consisting of a hearing assist device, neurostimulator, cardiac pacemaker, drug pump and cardiac defibrillator.

6. The header assembly of claim 1 wherein the intermediate conductor is a unitary member.

7. The header assembly of claim 1 wherein the sidewall comprising the body has spaced apart opposed portions and wherein the connection inlet extends to the bottom wall at both opposed portions of the sidewall.

8. A header assembly for connecting an implantable medical device to a conductor lead terminating at a body organ intended to be assisted by the medical device comprising a housing containing control circuitry, at least one electrical energy storage device, and at least one feedthrough wire extending from the control circuitry and through a wall of the housing, the header assembly comprising:
    a) a body mountable on the housing for the medical device, wherein the body has a sidewall extending to a bottom wall disposable immediately adjacent to the medical device housing and wherein a connection inlet is provided in the bottom wall;
    b) at least one terminal supported by the body, wherein the terminal is directly connectable to the conductor lead; and
    c) an intermediate conductor supported by the body, the intermediate conductor having a distal end connected to the terminal and a proximal end comprising an enlarged head having a bore into which the distal end of the feedthrough wire is receivable and connectable, wherein the enlarged head has a groove in communication with the bore, and a spring is nested in the groove so that when the feedthrough wire is received in the bore, the spring contacts the feedthrough wire.

9. The header assembly of claim 8 wherein the groove is an annular groove and the spring is an annular member supported in the groove to surround the feedthrough wire.

10. The header assembly of claim 8 wherein the spring is a leaf spring.

11. A method for connecting an implantable medical device to a conductor terminating at a body organ intended to be assisted by the medical device, comprising the steps of:
    a) providing the medical device having a housing containing control circuitry, at least one electrical energy storage device and at least one feedthrough wire extending from the control circuitry through a wall of the housing to a distal end located outside the housing;
    b) providing a body having a sidewall extending to a bottom wall and wherein a connection inlet is provided in the body sidewall extending to the bottom wall at the sidewall, the body supporting at least one terminal and at least one intermediate conductor, wherein the intermediate conductor has a distal end connected to the terminal and a proximal end comprising a step;
    c) mounting the body on the medical device with the distal end of the feedthrough wire residing in the Connection inlet in the body and disposed in a lapped relationship with the step at the proximal end of the intermediate conductor;
    d) connecting the distal end of the feedthrough wire to the proximal end of the intermediate conductor in a lap joint construction; and
    e) back filling a polymeric material in the connection inlet to prevent body fluids from coming into contact with the lap joint connection between the intermediate conductor and the feedthrough wire.

12. The method of claim 11 including providing the body of a polymeric material.

13. The method of claim 11 including providing the body comprising a first inlet that receives a bracket secured to the housing and a second inlet and including the step of mounting the header assembly on the medical device with the bracket received in the first inlet and moving a wedge into the second inlet and a bracket inlet thereby securing the header assembly to the medical device.

14. A header assembly for connecting an implantable medical device to a conductor lead terminating at a body organ intended to be assisted by the medical device comprising a housing containing control circuitry, at least one electrical energy storage device, and at least one feedthrough wire extending from the control circuitry and through a wall of the housing, the header assembly comprising:
  a) a body mountable on the housing for a medical device;
  b) at least one terminal supported by the body, and being directly connectable to the conductor lead; and
  c) an intermediate conductor supported by the body, the intermediate conductor having a distal end connected to the terminal and a proximal end comprising a step that is securable to the feedthrough wire in a lap joint construction.

15. A header assembly for connecting an implantable medical device to a conductor lead terminating at a body organ intended to be assisted by the medical device comprising a housing containing control circuitry, at least one electrical energy storage device, and at least one feedthrough wire extending from the control circuitry and through a wall of the housing, the header assembly comprising:
  a) a body mountable on the housing for a medical device;
  b) at least one terminal supported by the body, and being directly connectable to the conductor lead;
  c) an intermediate conductor supported by the body, the intermediate conductor having a distal end connected to the terminal and a proximal end directly connectable to the feedthrough wire; and
  d) wherein the body includes a first inlet that receives a bracket secured to the housing and a second inlet and wherein with the bracket received in the first inlet, a wedge is receivable in the second inlet and a bracket inlet to secure the header assembly to the medical device.

16. The header assembly of claim 15 wherein the bracket is either L-shaped or U-shaped.

17. A header assembly for connecting an implantable medical device to a conductor lead terminating at a body organ intended to be assisted by the medical device comprising a housing containing control circuitry, at least one electrical energy storage device, and at least one feedthrough wire extending from the control circuitry and through a wall of the housing, the header assembly comprising:
  a) a body mountable on the housing for the medical device, wherein the body has a sidewall extending to a bottom wall with a connection inlet provided in the body sidewall extending to the bottom wall at the sidewall, the bottom wall positionable immediately adjacent to the medical device housing, wherein the body includes a first inlet that receives a bracket secured to the housing and a second inlet and wherein with the bracket received in the first inlet, a wedge is receivable in the second inlet and a bracket inlet to secure the header assembly to the medical device;
  b) at least one terminal supported by the body, wherein the terminal is directly connectable to the conductor lead; and
  c) an intermediate conductor supported by the body, the intermediate conductor having a distal end connected to the terminal and a proximal end residing in the connection inlet in the body and there being directly connectable to the feedthrough wire.

18. The header assembly of claim 17 wherein the bracket is either L-shaped or U-shaped.

19. A header assembly for connecting an implantable medical device to a conductor lead terminating at a body organ intended to be assisted by the medical device comprising a housing of mating first and second clam shells in either an overlapping or butt welded construction and containing control circuitry, at least one electrical energy storage device, and at least one feedthrough wire extending from the control circuitry and through a wall of the housing, the header assembly comprising:
  a) a body mountable on the mating first and second housing clam shells in either the overlapping or butt welded construction, wherein the body has a sidewall extending to a bottom wall disposable immediately adjacent to the medical device housing and wherein a connection inlet is provided in the body sidewall extending to the bottom wall at the sidewall;
  b) at least one terminal supported by the body, wherein the terminal is directly connectable to the conductor lead; and
  c) an intermediate conductor supported by the body, the intermediate conductor having a distal end connected to the terminal and a proximal end residing in the connection inlet in the body and there being directly connectable to the feedthrough wire.

20. A method for connecting an implantable medical device to a conductor terminating at a body organ intended to be assisted by the medical device,: comprising the steps of:
  a) providing the medical device having a housing containing control circuitry, at least one electrical energy storage device and at least one feedthrough wire extending from the control circuitry through a wall of the housing to a distal end located outside the housing;
  b) providing a body having a sidewall extending to a bottom wall and wherein a connection inlet is provided in the bottom wall, the body supporting at least one terminal and at least, one intermediate conductor, wherein the intermediate conductor has a distal end connected to the terminal and a proximal end comprising an enlarged head having a bore comprising a groove supporting a spring;
  c) mounting the body on the medical device with the distal end of the feedthrough wire received in the bore of the enlarged head of the intermediate conductor residing in the connection inlet in the body with the spring contacting the feedthrough wire; and
  d) back filling a polymeric material in the connection inlet to prevent body fluids from coming into contact with the connect ion between the intermediate conductor and the feedthrough wire.

21. The method of claim 20 including providing the groove as an annular groove and the spring as an annular member supported in the groove surrounding the feedthrough wire.

22. The method of claim 20 including providing the spring as a leaf spring.

23. A method for connecting an implantable medical device to a conductor terminating at a body organ intended to be assisted by the medical device, comprising the steps of:
  a) providing the medical device having a housing containing control circuitry, at least one electrical energy storage device and at least one feedthrough wire extending from the control circuitry through a wall of the housing to a distal end located outside the housing;
  b) providing a body having a sidewall extending to a bottom wall and wherein a connection inlet is provided in the body sidewall extending to the bottom wall at the sidewall and including providing the body comprising a first inlet and a second inlet, the body supporting at least one terminal and at least one intermediate conductor, wherein the intermediate conductor has a distal end connected to the terminal and a proximal end;

c) securing the body on the medical device with the distal end of the feedthrough wire residing in the connection inlet in the body and disposed in a connectable relationship with the proximal end of the intermediate conductor and with the first inlet of the body receiving a bracket secured to the housing, and moving a wedge into the second inlet and a bracket inlet thereby securing the header assembly to the medical device;

d) connecting the distal end of the feedthrough wire to the proximal end of the intermediate conductor; and e) back filling a polymeric material in the connection inlet to prevent body fluids from coming into contact with the connection between the intermediate conductor and the feedthrough wire.

\* \* \* \* \*

UNITED STATES PATENT AND TRADEMARK OFFICE
CERTIFICATE OF CORRECTION

| | |
|---|---|
| PATENT NO. | : 7,167,749 B2 |
| APPLICATION NO. | : 10/701849 |
| DATED | : January 23, 2007 |
| INVENTOR(S) | : Biggs et al. |

It is certified that error appears in the above-identified patent and that said Letters Patent is hereby corrected as shown below:

Column 5, line 57, delete "10A" and insert --100A--.

Column 8, line 50, delete "Connection" and insert --connection--.

Signed and Sealed this

Fourteenth Day of December, 2010

David J. Kappos
*Director of the United States Patent and Trademark Office*